United States Patent
Cohen et al.

(10) Patent No.: US 12,064,271 B2
(45) Date of Patent: Aug. 20, 2024

(54) TISSUE PROPERTIES PRESENTATION SYSTEM AND METHOD

(71) Applicant: DILON MEDICAL TECHNOLOGIES LTD., Caesarea (IL)

(72) Inventors: Gil Cohen, Jerusalem (IL); Gal Aharonowitz, Sede Warburg (IL); Iddo Geltner, Even Yehuda (IL); Yoav Zur, Atlit (IL)

(73) Assignee: DILON MEDICAL TECHNOLOGIES LTD., Caesarea (IL)

( * ) Notice: Subject to any disclaimer, the term of this patent is extended or adjusted under 35 U.S.C. 154(b) by 797 days.

(21) Appl. No.: 17/268,740

(22) PCT Filed: Aug. 14, 2019

(86) PCT No.: PCT/IL2019/050909
§ 371 (c)(1),
(2) Date: Feb. 16, 2021

(87) PCT Pub. No.: WO2020/035860
PCT Pub. Date: Feb. 20, 2020

(65) Prior Publication Data
US 2021/0298691 A1 Sep. 30, 2021

Related U.S. Application Data

(60) Provisional application No. 62/764,765, filed on Aug. 16, 2018.

(51) Int. Cl.
*A61B 5/00* (2006.01)
*A61B 5/053* (2021.01)
(Continued)

(52) U.S. Cl.
CPC .............. *A61B 5/743* (2013.01); *A61B 5/053* (2013.01); *A61B 5/7435* (2013.01);
(Continued)

(58) Field of Classification Search
CPC ..... A61B 5/053; A61B 5/0531; A61B 5/0537; A61B 5/0538; A61B 5/74
See application file for complete search history.

(56) References Cited

U.S. PATENT DOCUMENTS

| 2003/0138378 A1 | 7/2003 | Hashimshony |
| 2009/0267945 A1 | 10/2009 | Warntjes et al. |

(Continued)

FOREIGN PATENT DOCUMENTS

| JP | 2005058730 A | 3/2005 |
| JP | 2013517040 A | 5/2013 |

(Continued)

*Primary Examiner* — Eric F Winakur
*Assistant Examiner* — Abel Seifu Abegaz
(74) *Attorney, Agent, or Firm* — BROWDY AND NEIMARK, P.L.L.C.

(57) ABSTRACT

System and method for presentation of tissue sensing data being collected from a tissue being measured are presented and configured for on-line as well as for off-line presentation of the tissue sensing data, the system comprising a device configured and operable to display a graphical user interface, the graphical user interface comprises at least one observation field and is configured to be responsive to the tissue sensing data comprising one or more sensing datum of measured tissue property value, to transform each measured tissue property value into virtual representation in the at least one observation field in the form of a parametric space of two different characteristic parameters of tissue corresponding to the measured tissue property value.

17 Claims, 6 Drawing Sheets

(51) Int. Cl.
*G06F 3/0484* (2022.01)
*G06F 3/0487* (2013.01)

(52) U.S. Cl.
CPC .......... *A61B 5/7475* (2013.01); *G06F 3/0484* (2013.01); *G06F 3/0487* (2013.01)

(56) References Cited

U.S. PATENT DOCUMENTS

| | | | |
|---|---|---|---|
| 2010/0317962 A1* | 12/2010 | Jenkins | A61B 18/18 600/411 |
| 2011/0264000 A1 | 10/2011 | Paul | |
| 2012/0123296 A1 | 5/2012 | Hashimshony et al. | |
| 2012/0306493 A1 | 12/2012 | Voigt et al. | |
| 2013/0231548 A1* | 9/2013 | Brown | A61B 5/004 600/407 |
| 2015/0305649 A1 | 10/2015 | Cohen et al. | |
| 2016/0223483 A1* | 8/2016 | Reitsma | G01N 33/483 |
| 2018/0280683 A1* | 10/2018 | Botzer | A61N 1/3622 |

FOREIGN PATENT DOCUMENTS

| | | | |
|---|---|---|---|
| WO | 2008/072238 A2 | 6/2008 | |
| WO | 2014009893 A1 | 1/2014 | |
| WO | WO-2014009893 A1 * | 1/2014 | ......... A61B 10/0283 |

* cited by examiner

TISSUE PROPERTIES PRESENTATION SYSTEM AND METHOD

TECHNOLOGICAL FIELD

The invention is in the medical devices field and relates specifically to a system for displaying of measured tissue property(ies).

BACKGROUND

Several medical examination procedures are currently used for characterizing tissue, e.g. for diagnosing certain disease/cancer. The doctor may order lab test(s), scan(s) or biopsy in order to characterize the tissue involved.

High or low levels of certain substances in the body can be a sign of disease/cancer. However, abnormal lab results are not a sure sign of disease/cancer. While being an important tool, doctors cannot rely on lab tests alone to diagnose disease/cancer.

Imaging procedures can help the doctor know whether an abnormal tissue (e.g. tumor) is present. These include for example, CT Scan, X-ray scan, Nuclear scan, Ultrasound and MRI.

In most cases, doctors need to do biopsy to be able to make diagnosis of the disease. In traditional biopsy procedures, the doctor removes one or more samples of suspected tissue under guidance of an imaging technique, such as Ultrasound. A pathologist then looks at the already extracted tissue under a microscope to characterize it. The tissue sample(s) may be removed in several ways such as by using a needle to withdraw tissue, or by performing a surgery.

Being an invasive procedure, biopsy should preferably be performed to withdraw as little as necessary tissue while still giving enough information about the extent of the disease/tumor inside the body.

WO2008072238, assigned to assignee of the present invention, describes a graphical user interface (GUI) including: (a) a group definition module adapted to accept a user input defining groups; (b) a data receiver operable to receive a plurality of individual measurement input datum indicative of status of a substrate; (c) a grouping module configured to assign each of the individual measurement input datum to one of the groups to produce grouped data; and (d) an output module adapted to output and present the grouped data to a user.

WO2014009893, also assigned to the assignee of the present invention, describes a graphical user interface configured for presenting information related to signals received from an array of sensors arranged in a predetermined spaced-apart relationship along a measurement axis, the presented information being in the form of an array of locations spaced-apart along an axis corresponding to the array of the sensors, and a corresponding array of measured data in association with the array of the locations, the array of measured data being indicative of signals received from the array of the sensors respectively, thereby providing an operator with information regarding a profile of a measured tissue profile along a tissue mass aligned with the array of sensors.

GENERAL DESCRIPTION

The present invention provides the doctor/medical staff with novel system and method for characterizing tissue being examined. The technique of the present invention assists the doctor/medical staff in on the spot decision making during tissue examination, e.g. during a biopsy procedure. The system of the present invention receives as an input online tissue sensing data indicative of one or more tissue properties, processes the sensing data and generates output data including one or more other tissue properties, and presents the output data to the doctor/medical staff in a graphical interface in a meaningful way, enabling the doctor/medical staff to decide about a course of action, such as a need for acquiring one or more tissue samples from a region under inspection in the body/tissue portion.

The system of the invention receives the tissue sensing data from one or more tissue characterization sensors connected to the system. The tissue characterization sensors measure and collect tissue sensing data indicative of one or more tissue properties, such as optical and/or acoustic and/or electrical tissue properties. In some embodiments, the tissue sensing data is indicative of electrical impedance of the tissue. Such tissue characterization sensors are described, for example, in US2003138378, US2012123296 and US2015305649, all assigned to the assignee of the present invention.

The system of the invention processes the input tissue sensing data and generates, as an output tissue data, two or more, specifically two, values of tissue characteristic parameters that are derived/calculated from the one or more measured tissue properties.

The output tissue data, being two or above-two dimensional, is presented to a user in a suitable observation field on a graphical interface, enabling the user to make a decision about the tissue being measured. For example, if the user is using a connected biopsy device carrying the tissue characterization sensors, the user will be able to make an online decision relating to acquisition of a sample of the tissue portion being measured. The output tissue data can be presented graphically, numerically or in both fashions.

It is noted that the presentation of the values of tissue characteristic parameters is not necessarily arranged in the observation field in relation with or connection to the respective measured locations in the tissue and/or order of measurements being taken If more than one tissue characterization sensor is used, the system is configured to distinguish between the different sensors, e.g. by allocating different graphical identifiers to the different sensors. The differentiation can be obtained graphically, for example, by color, and/or size, and/or shape of the displayed data.

The system is also configured to assist the user in the decision making by enabling the user to compare between the output tissue data and data representing known tissue types already/previously saved in the system. The system is configured with one or more saved tissue type maps, each tissue type map is constructed in the same parametric space as the output tissue data and identifies/defines one or more tissue types, such as fat tissue, types of malignant tissue, and the like.

The system is configured and operable to enable saving multiple arrays of the output tissue data measured and processed at different times (sequentially) during the measurement session, thereby saving history tissue sensing data, and to enable recalling by the user any one of the saved arrays. Saving the output tissue data can be automatic, or upon user input, or resulting from another action in the measurement session, e.g. if a biopsy device is used, the output tissue data can be saved automatically whenever the user operates the biopsy device to collect a tissue sample.

Thus, according to a broad aspect of the invention, there is provided a system configured and operable for presentation of tissue sensing data being collected, the system comprising a device having one or more hardware processors configured by machine-readable instructions to cause display of a graphical user interface on the device, the graphical user interface comprising at least one observation field and configured to be responsive to tissue sensing data, from a tissue being measured, comprising one or more sensing datum of measured tissue property, to transform each measured tissue property into virtual representation in said at least one observation field in the form of a parametric space of two different characteristic parameters of a tissue corresponding to the measured tissue property.

In some embodiments, the measured tissue property is electrical impedance and the two different tissue characteristic parameters include conductivity and permittivity values of the tissue being measured.

In some embodiments, the graphical user interface is configured and operable to be responsive to the tissue sensing data in real-time such that the virtual representation of the tissue sensing data is carried out in real-time in the at least one observation field.

In some embodiments, the graphical user interface is further configured and operable to be responsive to user input to present, in the at least one observation field, alone or together with the tissue sensing data, a user selected map of tissue types in the parametric space of the two different characteristic parameters of the tissue.

In some embodiments, the graphical user interface is configured and operable to be responsive to the tissue sensing data comprising a plurality of sensing datum measured from different locations in the tissue by a plurality of sensors and concurrently display the plurality of the sensing datum in the observation field.

In some embodiments, the system comprises a storage utility configured and operable for selectively storing the tissue sensing data based on a user input, an input from an external device connected to the system, or automatically. The graphical user interface may be configured and operable to be responsive to a user input to present, in the at least one observation field, at least some of the tissue sensing data stored in the storage utility, either alone or together with tissue sensing data being collected in real-time.

In some embodiments, the system comprises an indexing utility configured and operable to assign indexing data of one or more indices to each of the one or more sensing datum, the one or more indices being indicative of one or more measurement characteristics of each of the one or more sensing datum. The one or more measurement characteristics may include one or more of the following: time of measurement, origin of measurement, measurement session ID, acquisition of tissue sample being measured, and user defined tag. The storage utility may be configured and operable for selectively storing the tissue sensing data with the corresponding indexing data, based on a user input, an input from an external device connected thereto, or automatically.

In some embodiments, the graphical user interface is configured and operable to be responsive to a user input selecting one or more of the measurement characteristics, to present, in the at least one observation field, the tissue sensing data associated with at least the indexing data corresponding to the user selected measurement characteristic(s).

In some embodiments, the graphical user interface is configured and operable to be responsive to a user input selecting one of the measurement characteristics, to present, in the at least one observation field, all of the tissue sensing data associated with the selected measurement characteristic.

In some embodiments, the graphical user interface is configured and operable to be responsive to the one or more measurement characteristics and present the tissue sensing data with a distinguishing feature corresponding to each of the measurement characteristics. The distinguishing feature may include one or more of the following: shape, color and size of the virtual representation of the tissue sensing data. The graphical user interface may further comprise one or more additional observation fields for presenting to a viewer one or more of the following: the one or more distinguishing feature(s), numerical value of the two tissue characteristic parameters, and graphical representation of a connected external device.

In some embodiments, the graphical user interface is configured and operable to be responsive to value(s) of the measured tissue property of the tissue sensing data to dynamically define range of the parametric space presented in the observation field.

In some embodiments, the graphical user interface is configured and operable to be responsive to a user input selecting or defining one or more of the following:
range of the parametric space,
Partitioning of the parametric space into pre-defined regions,
associating different colors or shapes or sizes of the virtual presentations with pre-defined values or value ranges of the measured tissue property or at least one of the two different tissue characteristic parameters, and
presenting functions derived from the measured tissue property values.

According to another broad aspect of the invention, there is provided a method for presenting tissue sensing data being collected, the method comprising: receiving in real-time tissue sensing data comprising one or more sensing datum of measured tissue property value, transforming in real-time the measured tissue property value into a parametric space of two different characteristic parameters of a tissue, and virtually representing the parametric space in a corresponding observation field on a graphical user interface.

In some embodiments, the method further comprises receiving user input indicative of a user selected map of tissue types, and virtually presenting, in the observation field, the user selected map of tissue types in the parametric space of the two different characteristic parameters of the tissue.

In some embodiments, the method further comprises selectively storing the tissue sensing data based on at least one of the following: a user input, an input from an external device, or automatically. The method may further comprise presenting, in the observation field, at least some of the stored tissue sensing data, based on a user input.

In some embodiments, the method further comprises assigning indexing data of one or more indices to each of the one or more sensing datum, the one or more indices being indicative of one or more measurement characteristics of each of the one or more sensing datum. The one or more measurement characteristics may comprise one or more of the following: time of measurement, origin of measurement, measurement session ID, acquisition of tissue sample being measured, and user defined tag. The method may further comprise selectively storing the tissue sensing data with the corresponding indexing data, based on a user input, an input from an external device, or automatically. The method may further comprise receiving an input from a user for selecting one or more of the measurement characteristics, and presenting, in the observation field, the tissue sensing data associated with at least the indexing data corresponding to the user selected measurement characteristic(s). The method may further comprise receiving an input from a user for selecting one of the measurement characteristics, and presenting, in the observation field, all of the tissue sensing data associated with the selected measurement characteristic. The method may further comprise presenting the tissue sensing data with a distinguishing feature corresponding to each of the measurement characteristics. The distinguishing feature may be one or more of the following: shape, color and size of the virtual representation of the tissue sensing data. The method may comprise presenting, in one or more additional observation fields on the graphical user interface, one or more of the following: one or more distinguishing feature(s), numerical value of the two tissue characteristic parameters, and graphical representation of an external device providing the tissue sensing data.

In some embodiments, the method comprises dynamically defining range of the parametric space presented in the observation field based on value(s) of the measured tissue property of the tissue sensing data.

In some embodiments, the method further comprises receiving a user input selecting or defining one or more of the following:
- range of said parametric space,
- Partitioning of the parametric space into pre-defined regions,
- associating different colors or shapes or sizes of the virtual presentations with pre-defined values or value ranges of the measured tissue property or at least one of the two different tissue characteristic parameters, and
- presenting functions derived from the measured tissue property values.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
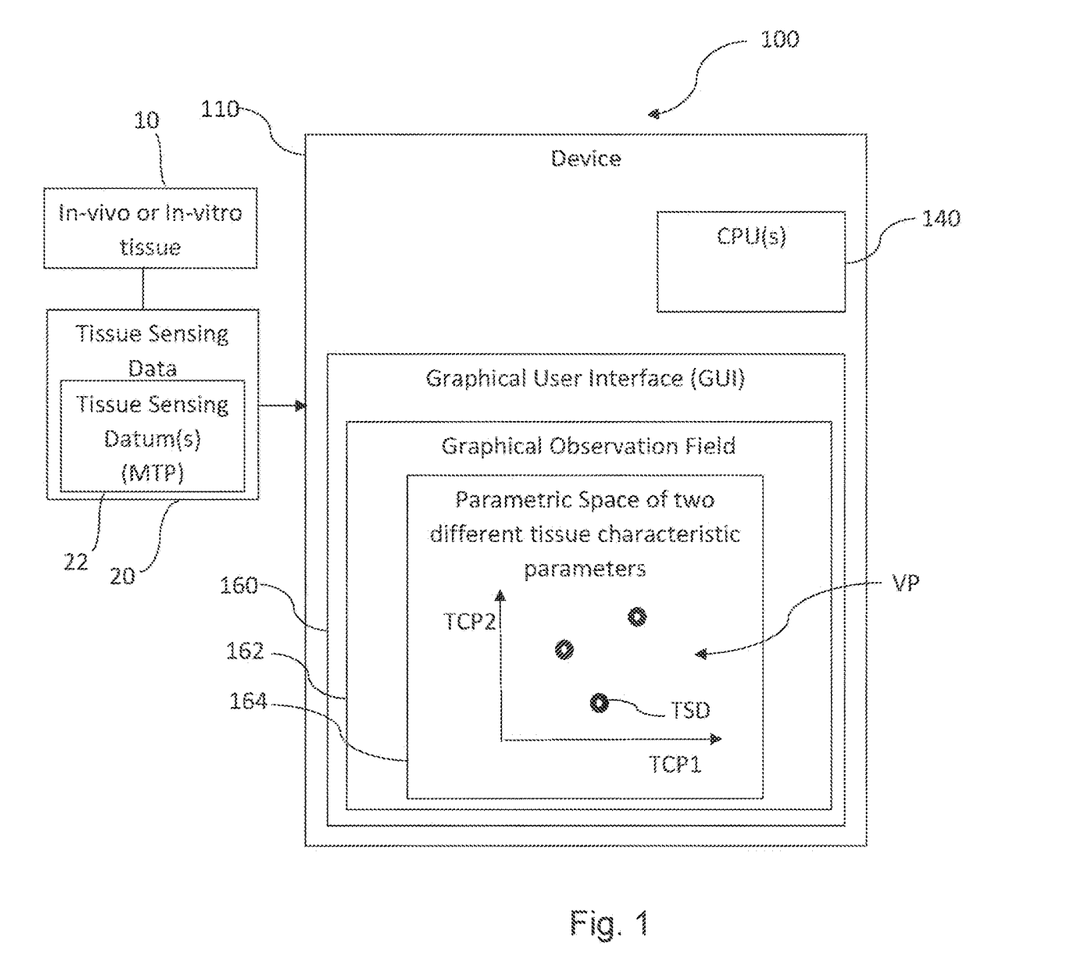
FIG. 1 illustrates by way of a block diagram an exemplary system according to a non-limiting embodiment of the present invention.

Reference is made to FIG. 1 illustrating a non-limiting example of a system 100 configured in accordance with the present invention. The system 100 is configured and operable for presenting tissue sensing data 20 being collected and includes a device 110 having one or more hardware processor units (CPU(s)) 140 configured to cause display of a graphical user interface 160 on the device. The graphical user interface 160 includes at least one observation field 162 and is configured to be responsive to the tissue sensing data 20 collected from the tissue 10 being measured in-vivo or in-vitro.

The tissue sensing data 20 includes one or more sensing datum(s) 22 of one or more measured tissue property MTP values. The device 110, by its CPU(s) 140 is configured and operable to transform each measured tissue property MTP value (represented by one tissue sensing datum) into virtual representation VP in the at least one observation field 162 in the form of a parametric space 164 of two different tissue characteristic parameters, TCP1 and TCP2, corresponding to the measured tissue property MTP value. In FIG. 1, three tissue sensing datum TSD are displayed in the parametric space 164.

The device 110 can be a dedicated hardware loaded with a specific firmware, or can alternatively be a generic computing device running a specifically designed program (software). The device 110 includes a display (not shown) capable of presenting the GUI 160 to a user. Generally, as will be detailed further below in FIG. 2, the device 110 includes an input utility configured for receiving input data including the tissue sensing data 20, the processing unit(s) 140 and an output utility configured for presenting the GUI 160. It is noted that, in some embodiments each of the utilities has its own CPU that controls its functionality, and in some other embodiments a single CPU may be connected to more than one utility/unit/module to control them. Therefore, the term CPU should be interpreted broadly, herein, meaning a controller/control unit and the like, and whenever a utility or a module is illustrated as configured to perform or be responsive to a certain action or process, it is equally meaning that the CPU controlling the specific utility or module is responsible for executing or being responsive to the mentioned action or process.

The device 110 can be configured, by the input utility and/or one or more of the CPU(s), to automatically identify at least a portion of the input data being the tissue sensing data 20. Additionally, the device 110 can be configured, by the input utility and/or one or more of the CPU(s), to automatically identify connection of an external device, carrying one or more tissue characterization sensors, to the system 100, to thereby receive therefrom sensing signals being indicative of the tissue sensing data 20. As mentioned, the tissue sensing data 20 includes one or more tissue sensing datum 22, each tissue sensing datum can be provided by a single sensor at a certain time. In case the tissue sensing data 20 includes a plurality of tissue sensing datum 22, they can be provided by a single sensor at a corresponding plurality of time points or by a plurality of sensors either simultaneously or sequentially at different times. The device 110 can also be configured to accept a user input via the input utility as will be further detailed below.

When tissue sensing data 20 is received at the device 110, the CPU(s) 140 process(es) the tissue sensing data 20, being indicative of one or more measured tissue properties MTP, and identify the tissue property(ies) being measured. In one non-limiting example, all the tissue sensing data is indicative of one measured tissue property. In another non-limiting example, the tissue sensing data is indicative of two or more measured tissue properties. As indicated above, the measured tissue property can be, for example, optical and/or acoustic and/or electrical property of the tissue. The CPU(s) 140 identifies each measured tissue property, typically received from a specific kind of tissue characterization sensor, and processes the relevant tissue sensing data in order to determine at least two different tissue characteristic parameters corresponding to the identified measured tissue property. For example, in case the measured tissue property is optical, the CPU(s) 140 is(are) configured to process the tissue optical data and determine, for example, two or more of the following: frequency, phase, intensity, absorbance, reflectance. In one specific non-limiting example, as will be further exemplified below with respect to FIG. 3, the measured tissue property is electrical impedance and the at least two different tissue characteristic parameters, calculated and determined by the CPU(s) are the conductivity and permittivity. The device 110, via the CPU(s) and/or the output utility (as described below), is configured for presenting one or more pairs of the determined tissue characteristic parameters, with a suitable (two-dimensional) parametric space, in the graphical observation field 162 of the graphical user interface 160, for each tissue sensing datum 22 received. In case more than one measured tissue property is identified in the received tissue sensing data (e.g., optical and acoustical measured tissue properties), a corresponding number of graphical observation fields may be generated on the graphical user interface, each field presenting two calculated/derived tissue characteristic parameters corresponding to each one of the identifiable measured tissue properties.

Figure 2:
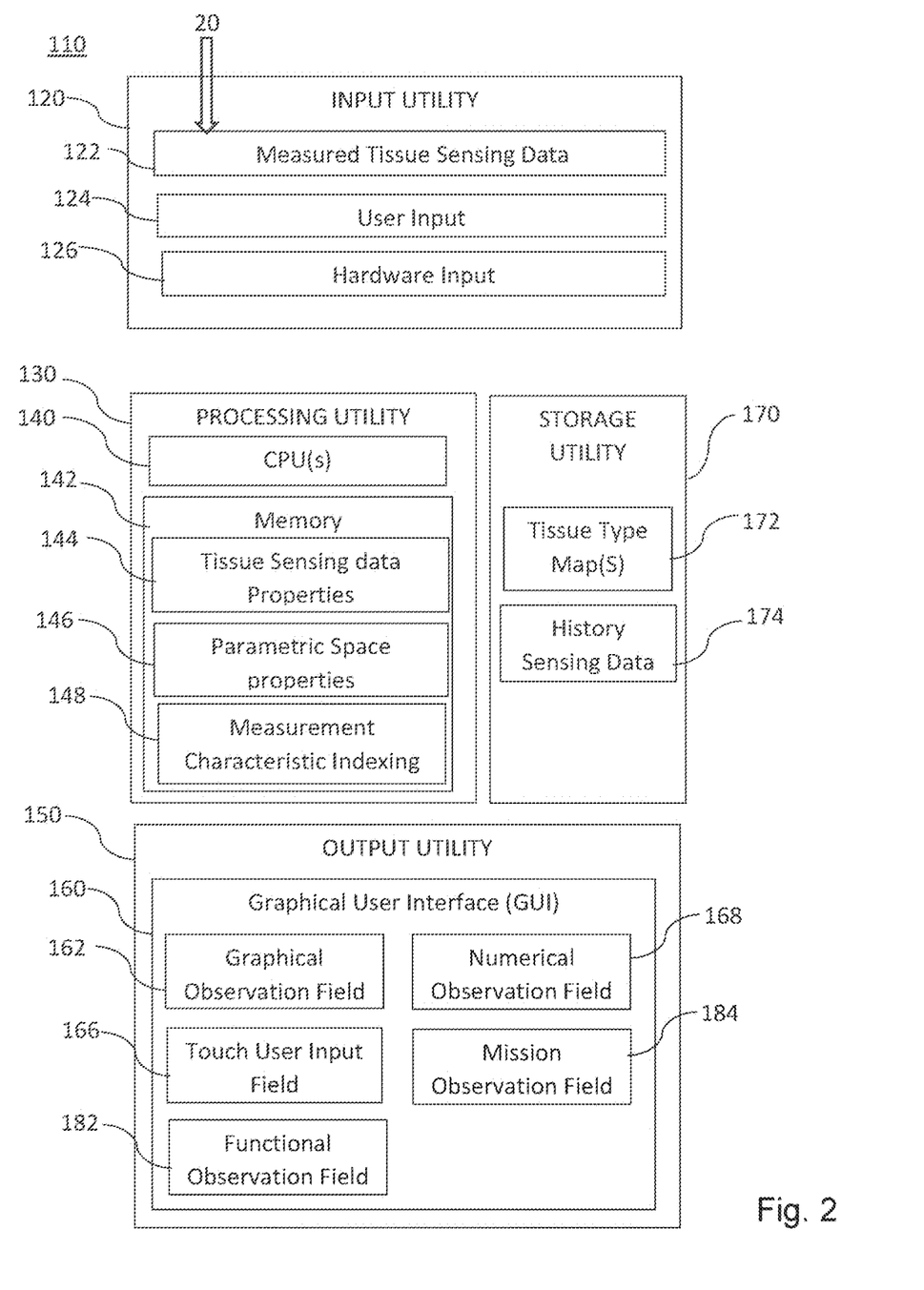
FIG. 2 illustrates by way of a block diagram exemplary features of the system of the invention according to non-limiting embodiments of the present invention.

Reference is now made to FIG. 2 illustrating in more details different utilities, modules and sub-modules of the device 110, some of them are optional, according to non-limiting embodiments of the present invention.

The device 110 generally includes an input utility 120, a processing utility 130 and an output utility 150. In addition, the device 110 includes a storage utility 170 for saving tissue sensing data or data indicative thereof and tissue type map(s), or can alternatively be configured with a network communication utility (not shown) enabling the device to access an external, remotely accessible, storage utility.

The input utility 120 includes a tissue sensing data module 122 configured and operable to accept as input the tissue sensing data 20 measured from a tissue portion (in-vivo or in-vitro), and a user input module 124 configured and operable to accept an input from a person using the device.

The tissue sensing data module 122 can be configured to automatically identify input data being the tissue sensing data 20. Additionally, the tissue sensing data module 122 can be configured to automatically identify connection of an external device, carrying one or more tissue characterization sensors, to the system 100, to thereby receive therefrom sensing signals being indicative of the tissue sensing data 20. The tissue sensing data module 122 may also be configured to distinguish between a plurality of tissue sensing datum collected by different tissue characterization sensors. The tissue sensing data module 122 is connected to the processing utility 130 and configured and operable to transmit the tissue sensing data to the processing utility 140 for processing.

The user input module 124 can be configured to accept user input in a variety of ways. In one non-limiting example, the user can use a keyboard, a mouse or other similar devices to input data to the device 110. In another non-limiting example, the user can use a touch interface to input data to the device 110, the touch interface can be configured as a touch user input field 166 that forms part of or is embedded in the graphical user interface 160. In yet another non-limiting example, the user can use audio interface (not specifically illustrated) to input data to the device 110. The user input module 124 can be used to enter various user inputs relating to the information and data presented on the GUI 160, as will be further detailed below.

The processing utility 130 includes the CPU(s) 140 that can be distributed in more than one location/utility (in case a plurality of CPUs exist in the device). Each CPU is configured and operable to process and execute the various actions needed to receive and process the measured tissue sensing data 20 in order to cause presentation of the processed (calculated/derived) at least two different tissue characteristic parameters in a suitable parametric space in the GUI 160. The processing utility 130 also includes a memory 142, in the form of a non-transitory and/or RAM memory, being configured and operable to save machine-readable instructions related to the processing and presentation of the tissue sensing data, as will be further described below.

The output utility 150 may be configured as or includes a display device configured for displaying the GUI 160 to the user. The GUI 160 includes one or more graphical observation fields 162 each configured, as described above, for displaying a parametric space of two different tissue characteristic parameters, for each measured tissue property received by the input utility 120. Additionally, the GUI 160 may include one or more fields 166 for accepting user input by touch, and one or more numerical observation field(s) 168 configured for displaying numerical values of the at least two different tissue characteristic parameters, e.g. in a list form, such that each row displays the at least two different tissue characteristic parameters originating from a specific tissue characterization sensor.

The device 110 is generally configured for displaying the tissue sensing data on the GUI 160 in real-time, enabling real-time decision making such as deciding on tissue acquisition during a biopsy procedure. However, the device 110 can also be configured for saving the tissue sensing data, collected in each measurement session, for future reference and display, upon a user input, in an off-line mode. As such, the storage utility 170 includes a history sensing data module 174 configured for saving the received raw measured tissue sensing data, and/or the processed (calculated) at least two tissue characteristic parameters. The user can be then able to select, using a suitable user input, one or more of the saved tissue sensing data acquired during different time points in one or more measurement sessions, for display in the GUI. In some embodiments, the storage utility 170 is configured to be responsive to a user input to save one or more tissue sensing data being collected. In some embodiments, the input utility 120 includes a hardware input module 126 configured to identify and receive an input from a connected hardware, such as a biopsy device, and the storage utility 170 is configured to be responsive to the hardware input to save one or more tissue sensing data being collected. For example, during a biopsy procedure, collection of a tissue sample by a suitable movement of a part in the biopsy device can be identified by the hardware input module 126 as an act that initiates data saving and instructs the storage utility 170 (e.g. via a CPU 140 in the device) to save the tissue sensing data collected just prior to the tissue sample acquisition. Alternatively, the device 110 can be configured such that all the measured tissue sensing data, during a measurement session, is saved, automatically or upon a user input, in the storage utility 170. The user can then access the saved data and selectively display the saved data, whether alone or in combination with real-time data, on the GUI 160. The user can choose to display the data in various ways, as will be further described below, for example displaying some or all tissue sensing datum collected substantially concurrently (within a defined short time slot) by a plurality of tissue characterization sensors, or displaying some or all tissue sensing datum collected by the same tissue characterization sensor at different times.

The storage utility 170 may also include a tissue type map module 172 configured and operable to store one or more tissue type maps that can be displayed on the GUI 160 upon a user input or automatically based on the kind of the tissue sensing data being measured and/or the measurement session running. Each tissue type map includes one or more tissue types with their tissue characteristic parameters values matching the parametric space displayed on the GUI 160. For example, if the parametric space displayed on the GUI 160 includes such tissue characteristic parameters as conductivity and permittivity, one saved tissue map can include one or more pairs of conductivity and permittivity values corresponding to respective one or more tissue types, such as conductivity and permittivity values for fat tissue, muscle tissue, etc. This way, by displaying the tissue type map on the GUI, alone or together with the real-time collected tissue data, the user can make on-line decisions relating to the tissue being measured, such as applying localized treatment to tissue and/or collecting one or more tissue samples for further examination in the lab. The user can select one map among a plurality of maps stored in the storage utility, or can on his own enter a map for display on the GUI.

The device 110 can also include, as part of the processing utility 130, a measurement characteristic indexing module 148 configured and operable to tag each one of the measured tissue sensing datum with one or more tags (indices) indicative of one or more measurement characteristics. The tagging/indexing can be performed in real-time or at a subsequent stage. Generally, at least some of the tagging is done in real-time. Non-limiting examples of the measurement characteristics that can be assigned to each received tissue sensing datum include: time of measurement; origin of measurement (i.e. the tissue characterization sensor supplying the tissue sensing datum); tissue sampling act corresponding to the specific tissue sensing datum, i.e. whenever a tissue sample is collected by a biopsy device connected to the system 100 a suitable tag is assigned to the tissue sensing datum measured just before the tissue sampling. Additionally, the device may be configured to receive a user input defining a tag to be allocated to the tissue sensing datum. In one non-limiting example, the user can tag the received tissue sensing data by a name (ID) of the measurement session. The one or more indices assigned to the tissue sensing datum can be saved together with the tissue sensing datum, enabling the user to select and choose one or more measurement characteristics and to immediately or retroactively display, in the GUI 160, the tissue sensing datum corresponding to the measurement characteristic(s) chosen.

The following are non-limiting examples of user selections of measurement characteristics: selecting a time slot in which all the tissue sensing data collected are displayed; selecting one or more tissue characterization sensors to display the tissue sensing data originating therefrom in a specific measurement session, during a defined time slot or in all the measurement sessions. The touch user input field 166 can be configured to enable the user selection of the measurement characteristics, e.g. measurement session IDs defined as numbers, tissue characterization sensors defined as numbers or logos or visual distinguishing features.

The processing utility 130 may also include machine-readable instructions enabling the user to apply, or which are applied automatically based on another input (whether from the user or from a connected hardware (e.g. via the hardware input module 126)), to thereby manage the data presentation on the GUI 160. In one non-limiting example, the properties of the parametric space, for each of the involved tissue characteristic parameters displayed, can be determined through a parametric space properties module 146. For example, the range and/or the units and/or the presentation method (Cartesian, polar, etc.) can be determined and displayed automatically and dynamically (by the GUI) based on the received and presented tissue sensing data and/or calculated/derived tissue characteristic parameters, or can be determined beforehand or during the measurement session by the user. In another non-limiting example, the parametric space can be partitioned into pre-defined regions to assist in the data presentation and/or interpretation. The partitioning may be enhanced by the use of different colors for the different regions.

A tissue sensing data properties module 144 of the processing utility enables the user and/or the system (and the GUI) to assign a distinguishing feature for each tissue sensing datum presented on the GUI 160. For example, different tissue sensing datum can be assigned different shapes and/or different colors and/or different sizes of the virtual presentation, to enable the user to distinguish between the different tissue sensing datum, whether displayed concurrently or sequentially on the GUI. For example, the shape and/or color and/or size of the virtual representation of each tissue sensing datum can be unique and different from the other tissue sensing datum, enabling the user to differentiate between the different tissue sensing datum presented. Non-limiting examples of using the distinguishing presentation features include: displaying different tissue sensing datum originating from respective different tissue characterization sensors in different shapes and/or different colors and/or different sizes. Specifically, only one of the shape or color or size distinguishing features can be changed to differentiate between the displayed tissue sensing datum. Furthermore, the tissue sensing data properties module 144 may also enable the user, via a suitable user input, to determine threshold value(s) of the displayed tissue sensing data such that tissue sensing datum value above or below the threshold value is presented on the GUI with a distinguishing feature being its shape, color or size. Additionally, the tissue sensing data properties module 144 may also enable the user, via a suitable user input, to select built-in or define functions of the measured and/or calculated/derived tissue characteristic parameters. The functions, being in equation or graph form, can then be displayed in a functional observation field 182 on the GUI 160.

The tissue sensing data properties module 144 also enables the user, via a suitable user input, to determine which measured tissue properties or tissue characteristic parameters are to be displayed on the GUI, whether in real-time or retroactively in the off-line mode. For example, if the measured tissue property is the optical response, the user can decide to display any two or more of the following tissue characteristic parameters: optical absorbance, optical reflectance, optical transmission, and each of the aforementioned properties/characteristic parameters can be displayed in the intensity or frequency domains.

The GUI 160 may have additional observation fields responsive to actions relating to the tissue examination procedure. A mission observation field 184 on the GUI 160 may be used to display, either automatically or manually upon a user input, a graphical representation of an external tissue treatment device once connected to the device 110. For example, the mission observation field 184 may display a graphical representation of a biopsy device with or without a tissue characterization sensor array mounted thereon. The tissue characterization sensors can be presented with the same distinguishing feature used to differentiate between the tissue sensing datum in the parametric space on the graphical observation field 162.

Reference is now made to FIGS. 3A-3G illustrating a non-limiting example of a GUI with various observation fields according to some embodiments of the present invention. The present example illustrates some of the features of the device when used with a biopsy device carrying an array of tissue characterization sensors which are configured and operable for sensing the tissue electrical impedance property. To facilitate description of the various options of the exemplified GUI, features and elements similar to the above described features and elements of device 110 and GUI 160 will be given similar reference numbers with a difference of 100. For example, the number 260 presents a GUI and the number 264 presents the parametric space displayed on the GUI 260.

Figure 3A:
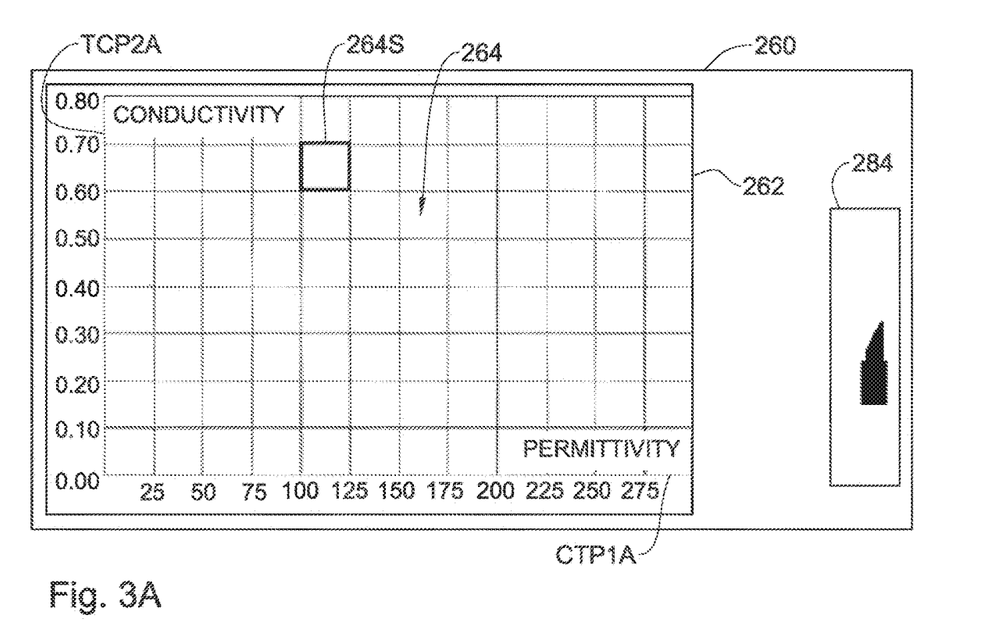
FIGS. 3A-3G exemplify a graphical user interface incorporating exemplary non-limiting features of the system of the present invention.

FIG. 3A illustrates a GUI 260 configured with one or more graphical observation field(s) 262 (one is shown) that include(s) parametric space 264 in the form of Cartesian coordinates of two calculated tissue characteristic parameters TCP1A and TCP2A, being permittivity (on the x-axis) and conductivity (on the y-axis). As described above, the TCP1A and TCP2A can be defined by the user or in some cases can be displayed automatically based on identification of the specific external device connected to the system. As shown, the two-dimensional parametric space 264 is also partitioned by grid lines (which is optional), defining squares 264S used to visually assist a user in localization and/or interpretation of tissue sensing datum that will be displayed in the parametric space. Also shown is a mission observation field 284 that displays a graphical presentation of an external biopsy device connected to the system of the invention. The mission observation field 284 of the GUI 260 can be configured to reflect the actual state of the connected external device. In this instance, the GUI is shown at the start of a tissue biopsy examination procedure in which the device is still in its closed position. The graphical representation of the biopsy device can be dynamic and follows the different on-line states of the biopsy device during a measurement session, as will be further described below.

Figure 3B:
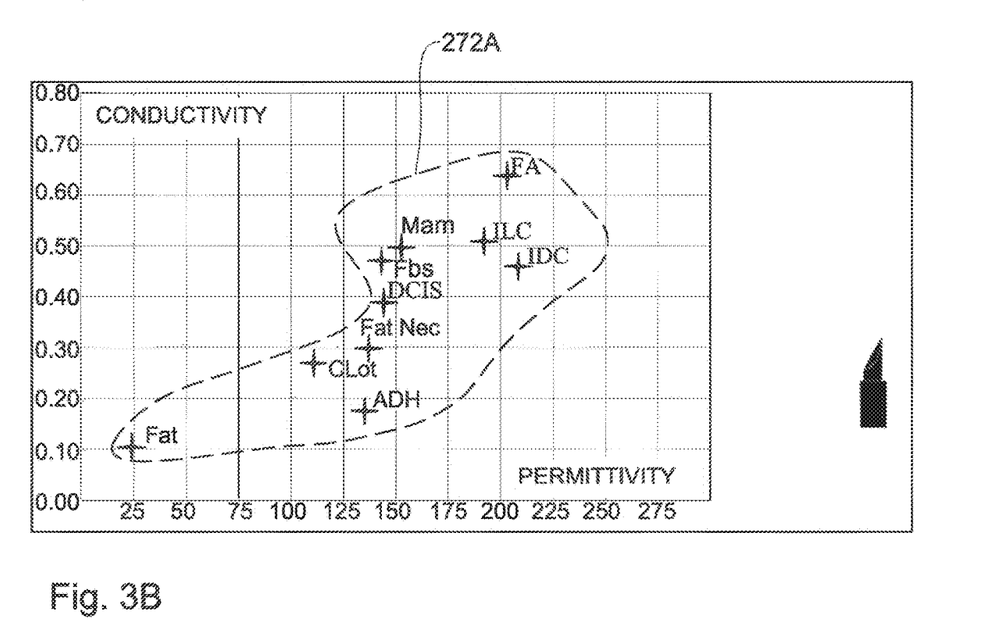

FIG. 3B illustrates the GUI 260 displaying, typically based on a user selection and input, or alternatively automatically by the processing utility 130 based on input data provided by the user or the connected hardware, a tissue type map 272A which is usually stored in the storage utility 170. As shown in this example, the displayed tissue type map includes a plurality of conductivity-permittivity value pairs corresponding to different tissue types within the breast. The conductivity-permittivity value pairs corresponding to the different tissue types are obtained, for example, from values reported in the literature, or from previous measurements performed and saved in the storage utility 170. The conductivity-permittivity value pairs corresponding to different tissue types help the user while navigating with the biopsy device carrying the tissue characterization sensors to identify the examined tissue.

Figure 3C:
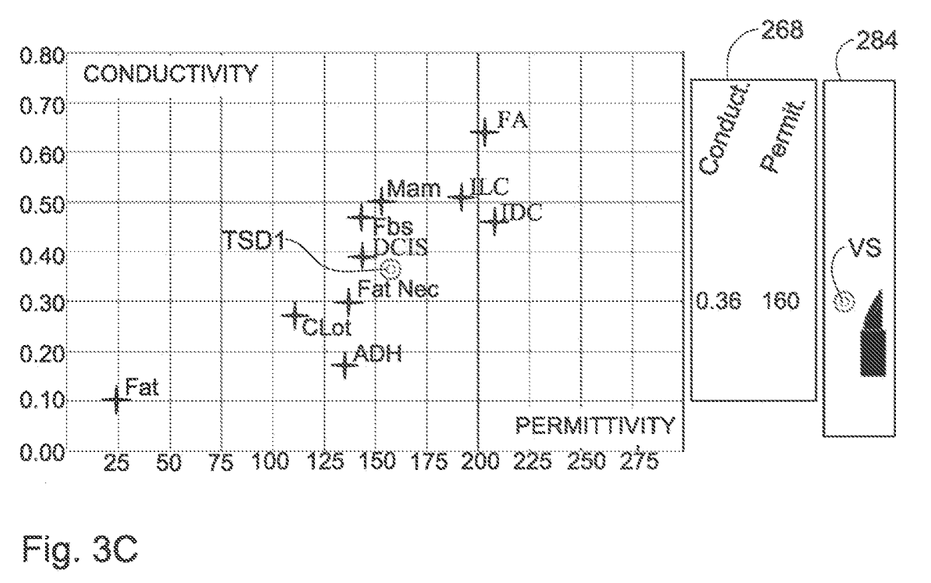

FIG. 3C illustrates the start of the tissue characterization procedure by the connected biopsy device. The biopsy device is still in its closed state and carries one tissue characterization sensor on its tip, a virtual sensor representation VS of the sensor's location on the biopsy device is shown beside the device representation in the mission observation field 284. The tissue sensing datum TSD1 measured by the tissue characterization sensor is displayed on the parametric space 264 with a shape matching the shape of the virtual representation of the sensor VS. Also shown in the figure, is a numerical observation field 268 in which the values of the tissue characteristic parameters—the permittivity and the conductivity—of the TSD1 are displayed beside the virtual representation of the sensor VS. As the user navigates with the biopsy device inside the examined tissue, the values of the tissue characteristic parameters, the permittivity and conductivity, may change and the location of the TSSD1 in the parametric space changes accordingly.

Figure 3D:
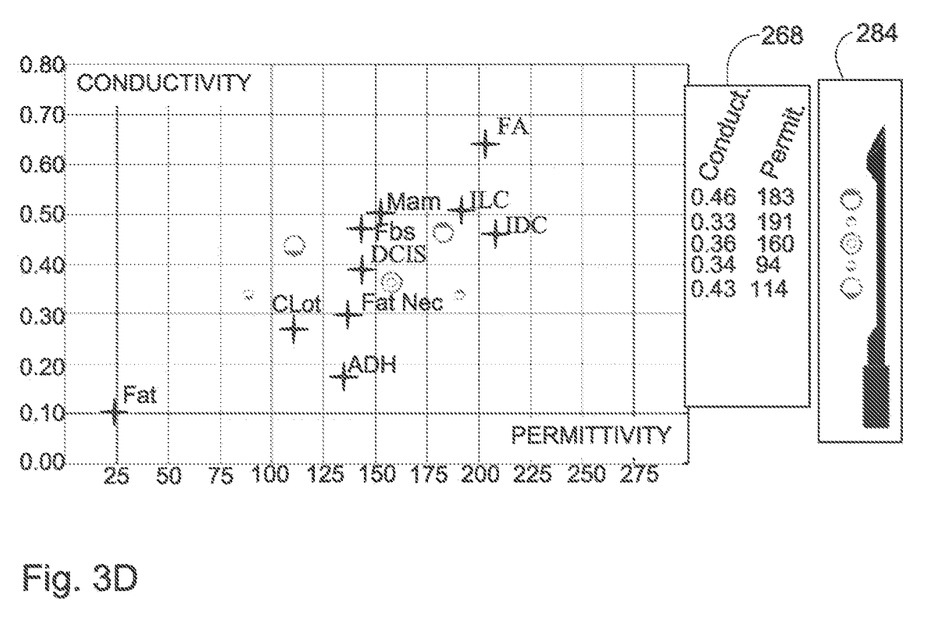

FIG. 3D illustrates an open state of the biopsy device in which a plurality of tissue characterization sensors carried thereby are active and are virtually represented beside the device in the mission observation field 284. In this specific example, the biopsy device includes five sensors, in addition to the tip sensor which is not shown now because it is not active in the open state of the biopsy device. As shown, each sensor is represented by a different shape to distinguish between them. Each sensor generates a TSD which is displayed in the parametric space together with the tissue type map. The numerical observation field also displays a list of five lines, where each line includes values of permittivity and conductivity and is displayed beside the respective sensor.

It should be noted that the GUI may be configured to adapt to the sensor configuration on the used biopsy device. For example, the biopsy device my not have a tissue characterization sensor on its tip. In this case, the GUI screen of FIG. 3C will not be part of the GUI In another example, there may be more, or less, sensors on the biopsy needle in the open configuration shown in FIG. 3D.

Figure 3E:
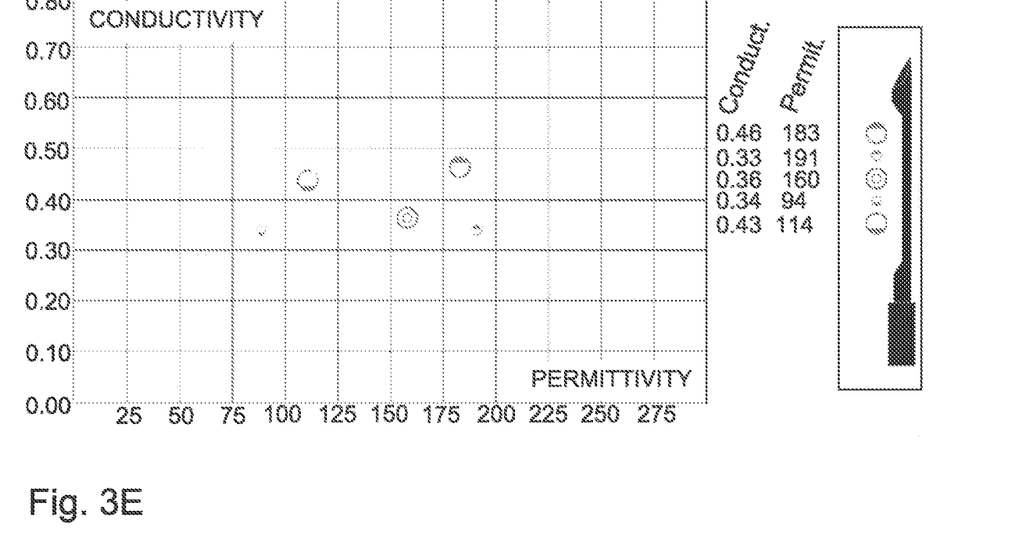

FIG. 3E exemplifies how the user can activate or deactivate the display of the tissue type map together with the display of the on-line tissue sensing data.

Figure 3F:
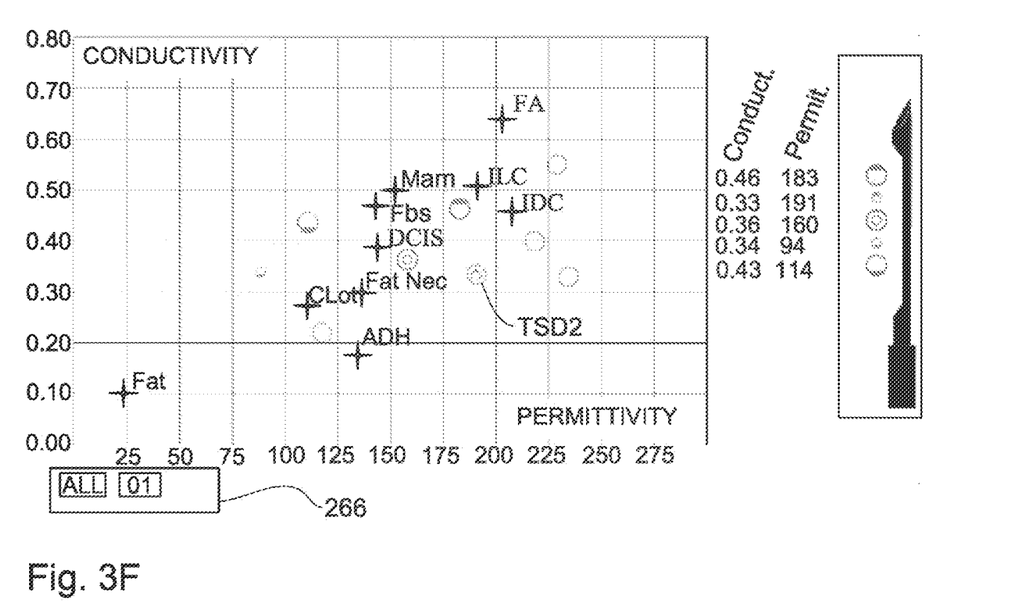

FIG. 3F illustrates the feature of saving the tissue sensing data in the storage utility 170, either automatically or manually by an input from the user, during a measurement session, and selectively displaying saved data together with on-line measured tissue sensing data. As shown, the already saved data can be displayed, upon a user selection and input via dedicated touch buttons, numbered with simple numbers indicating groups of saved data, in the touch user input field 266. As shown, the online-data is displayed with each tissue sensing datum, originating from a different tissue characterization sensor, having a different shape, while all the previously collected and saved five tissue sensing datum are displayed with the same shape, for example a circle. As described above, each measured and saved tissue sensing datum is tagged with one or more measurement characteristics. In this example, the user chooses the biopsy taking event (tissue sampling act) indexing for displaying the saved data. In another example, the user may choose the time of measurement indexing for displaying the saved data. In other words, all the tissue sensing datum saved during a previous measurement session or during a time slot in the measurement session, are displayed. Therefore, all the saved data are presented with the same shape. If, however, in another example, the user chooses also the origin of measurement characteristic to be displayed, then the different saved tissue sensing datum may be displayed with different shapes to indicate the sensor by which the tissue sensing datum was collected. Additionally, the saved data and the online data can be displayed with different colors, to further facilitate user understanding of the displayed data. One of the uses for displaying saved data together with on-line data is to help a user come back to a specific measured location in the tissue in case the tissue location is medically important, and by this enable the user to treat or sample the tissue at that location. Such ability of the system is illustrated in the figure by the tissue sensing datum TSD2. As shown, a value of online datum from the second sensor (when the five sensors are counted from above downwards) coincides with a saved value of datum measured by one of the sensors. Another use for displaying saved data together with on-line data is to help a user assess whether specific types of tissue have been already sampled, in order to evaluate if there is a need to take additional biopsy samples from the current instantaneous (real-time) locations of the biopsy device.

Figure 3G:
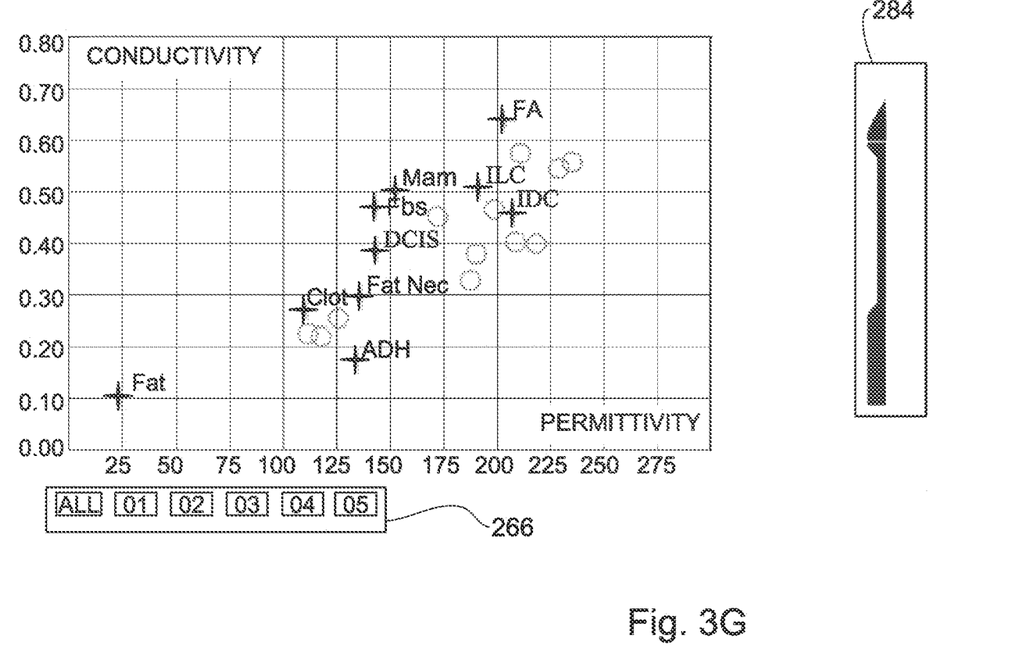

FIG. 3G exemplifies the ability of a user to use the touch user input field 266 in order to select a plurality of saved data groups for concurrent display in the parametric space in the graphical observation field. This is an off-line mode/state in which no signals are arriving from any of the sensors which are inactive as illustrated in the mission observation field 284. As shown, five groups of tissue sensing data, numbered 01-05, have been saved already, and the user can select any of the groups or any combination thereof for display in the parametric space. In the shown example, the user selected the highlighted saved groups 01 and 03 for display.

It should be understood that the off-line mode can also be implemented without a biopsy device connected, or by using a hardware configuration (e.g. a computing device such as a tablet, desktop, laptop) with no connection to a biopsy device, or not being configured for receiving tissue sensing data. The saved data groups analyzed off-line are retrieved from the storage utility 170.

Accordingly, the present invention provides a user with a comprehensive tool for on-line as well as off-line data display in ways that assist the user in decision making for tissue diagnosis and/or treatment.

The invention claimed is:

1. A system for helping a user to make on-line decisions during a medical procedure relating to a tissue being measured, configured and operable for presentation of tissue sensing data being collected, the system comprising a device having one or more hardware processors configured by machine-readable instructions to cause displaying of a graphical user interface on the device, the graphical user interface comprising at least one observation field and said one or more hardware processors further being configured to be responsive in real time to tissue sensing data, from said tissue being measured, comprising one or more sensing datum of measured tissue property value, and configured to transform in real-time each measured tissue property value into a virtual real-time representation in said at least one observation field in the form of a parametric space of two different tissue characteristic parameters; wherein said graphical user interface is further configured and operable to be responsive to user input to present in real-time, in said at least one observation field, together with said tissue sensing data, a user selected map of tissue types in said parametric space of the two different tissue characteristic parameters.

2. The system of claim 1, wherein said measured tissue property is electrical impedance, and said two different tissue characteristic parameters are conductivity and permittivity values of the tissue being measured.

3. The system of claim 1, where said one or more hardware processors are configured and operable to be responsive to the tissue sensing data comprising a plurality of sensing datum measured from different locations in the tissue by a plurality of sensors and said graphical user interface is configured to concurrently display said plurality of the sensing datum in said observation field.

4. The system of claim 1, comprising a storage utility configured and operable for selectively storing said tissue sensing data based on a user input, an input from an external device connected thereto, or automatically; wherein said graphical user interface is configured and operable to be responsive to a user input to present, in said at least one observation field, at least some of the tissue sensing data stored in the storage utility, either alone or together with the tissue sensing data being collected in real-time.

5. The system of claim 4, wherein the one or more processors are further configured by machine-readable instruction to include an indexing utility to assign indexing data of one or more indices to each of said one or more sensing datum, the one or more indices being indicative of one or more measurement characteristics of each of said one or more sensing datum; the one or more measurement characteristics comprise one or more of the following: time of measurement, origin of measurement, measurement session ID, acquisition of tissue sample being measured, and user defined tag; wherein said storage utility is configured and operable for selectively storing said tissue sensing data with the corresponding indexing data, based on a user input, an input from the external device connected thereto, or automatically; and wherein said graphical user interface is configured and operable to be responsive to a user input selecting one or more of said measurement characteristics, to present, in said at least one observation field, at least said tissue sensing data associated with the indexing data corresponding to the user selected measurement characteristic(s).

6. The system of claim 5, wherein said graphical user interface is configured and operable to be responsive to said one or more measurement characteristics and present said tissue sensing data with a distinguishing feature corresponding to each of said measurement characteristics, wherein said distinguishing feature comprises one or more of the following: shape, color and size of the virtual representation of the tissue sensing data.

7. The system of claim 6, wherein said graphical user interface further comprises one or more additional observation fields for presenting to a viewer one or more of the following: said one or more distinguishing feature(s), numerical value of said two tissue characteristic parameters, and graphical representation of a connected external device.

8. The system of claim 1, wherein said one or more hardware processors are configured and operable to be responsive to value(s) of said measured tissue property of said tissue sensing data to dynamically define range of said parametric space presented in said observation field.

9. The system of claim 1, wherein said graphical user interface is configured and operable to be responsive to a user input selecting or defining one or more of the following:
partitioning of the parametric space into pre-defined regions,
associating different colors or shapes or sizes of the virtual presentations with pre-defined values or value ranges of the measured tissue property or at least one of the two different tissue characteristic parameters, and
presenting functions derived from the measured tissue property values.

10. A method for helping a user to make on-line decisions relating to tissue being measured, by presenting in real-time tissue sensing data being collected, the method comprising: receiving in real-time, via one or more hardware processors, tissue sensing data comprising one or more sensing datum of measured tissue property value, transforming in real-time, via said one or more hardware processors, the measured tissue property value into a parametric space of two different characteristic tissue parameters calculated from the measured tissue property, and virtually representing in real-time said parametric space in a corresponding observation field on a graphical user interface; wherein said graphical user interface is further configured and operable to be responsive to user input to present in real-time, in said at least one observation field, together with said tissue sensing data, a user selected map of tissue types in said parametric space of the two different tissue characteristic parameters.

11. The method of claim 10, wherein said measured tissue property is electrical impedance and said two different tissue characteristic parameters are conductivity and permittivity values of the tissue being measured.

12. The method of claim 10, further comprising selectively storing said tissue sensing data based on at least one of the following: a user input, an input from an external device, or automatically, and selectively presenting, in said observation field, at least some of said stored tissue sensing data, based on a user input.

13. The method of claim 12, further comprising assigning indexing data of one or more indices to each of said one or more sensing datum, the one or more indices being indicative of one or more measurement characteristics of each of said one or more sensing datum, the one or more measurement characteristics comprise one or more of the following: time of measurement, origin of measurement, measurement session ID, acquisition of tissue sample being measured, and user defined tag; the method further comprising selectively storing said tissue sensing data with the corresponding indexing data, based on a user input, an input from an external device, or automatically, and receiving an input from a user for selecting one or more of said measurement characteristics, and presenting, in said observation field, at least said tissue sensing data associated with the indexing data corresponding to the user selected measurement characteristic(s).

14. The method of claim 13, further comprising presenting said tissue sensing data with a distinguishing feature corresponding to each of said measurement characteristics, the distinguishing feature comprising one or more of the following: shape, color and size of the virtual representation of the tissue sensing data.

15. The method of claim 14, comprising presenting, in one or more additional observation fields on the graphical user interface, one or more of the following: said one or more distinguishing feature(s), numerical value of said two tissue characteristic parameters, and graphical representation of an external device providing the tissue sensing data.

16. The method of claim 10, comprising dynamically defining range of said parametric space, via said one or more hardware processors, presented in said observation field based on value(s) of said measured tissue property of said tissue sensing data.

17. The method of claim 10, further comprising receiving a user input selecting or defining one or more of the following:
- partitioning of the parametric space into pre-defined regions,
- associating different colors or shapes or sizes of the virtual presentations with pre-defined values or value ranges of the measured tissue property or at least one of the two different tissue characteristic parameters, and
- presenting functions derived from the measured tissue property values.

* * * * *